(12) United States Patent
Sugimura et al.

(10) Patent No.: US 9,410,125 B2
(45) Date of Patent: Aug. 9, 2016

(54) MEDIUM FOR MAMMALIAN SOMATIC CELLS AND ADDITIVE THEREFOR

(75) Inventors: Itsuro Sugimura, Kobe (JP); Yoshiyuki Hotta, Tokyo (JP); Harumi Yamaguma, Osaka (JP)

(73) Assignee: FUJIREBIO INC., Tokyo (JP)

( * ) Notice: Subject to any disclaimer, the term of this patent is extended or adjusted under 35 U.S.C. 154(b) by 0 days.

(21) Appl. No.: 13/523,581

(22) Filed: Jun. 14, 2012

(65) Prior Publication Data

US 2012/0329155 A1 Dec. 27, 2012

(30) Foreign Application Priority Data

Dec. 28, 2007 (JP) ................... 2007-340802
Jun. 10, 2008 (JP) ................... 2008-151295

(51) Int. Cl.
*C12N 5/02* (2006.01)
*C12N 5/00* (2006.01)
*C12N 5/0775* (2010.01)

(52) U.S. Cl.
CPC ............ *C12N 5/0663* (2013.01); *C12N 5/0667* (2013.01); *C12N 2500/36* (2013.01); *C12N 2501/825* (2013.01)

(58) Field of Classification Search
CPC .............. C12N 5/0663; C12N 5/0667; C12N 2500/36; C12N 2501/825
See application file for complete search history.

(56) References Cited

U.S. PATENT DOCUMENTS

| 5,908,782 A | 6/1999 | Marshak et al. | |
|---|---|---|---|
| 2003/0211604 A1* | 11/2003 | E. Brown | 435/366 |
| 2010/0279412 A1* | 11/2010 | Kato et al. | 435/384 |

OTHER PUBLICATIONS

Bagga et al., Lysophosphatidic acid accelerates the development of human mast cells, Blood, Dec. 15, 2004_vol. 104, No. 13.*
Buznikov et al., Serotonin and serotonin-like substances as regulators of early embryogenesis and morphogenesis, Cell Tissue Res (2001) 305:177-186.*
Ganz et al., Effects of mitogens and other agents on rat mesangial cell proliferation, pH, and Ca2+, Am J Physiol. Aug. 1990;259(2 Pt 2): F269-78.*
Armstrong, Growth factor modulation of the extracellular matrix, Experimental Cell Research 288 (2003) 235-245.*
Doucet et al., Platelet Lysates Promote Mesenchymal Stem Cell Expansion: A Safety Substitute for Animal Serum in Cell-Based Therapy Applications, Journal of Cellular Physiology 205:228-236 (2005).*
Budisavljevic et al., Oxidative stress in the pathogenesis of experimental mesangial proliferative glomerulonephritis, Am J Physiol Renal Physiol 285: F1138-F1148, 2003.

(Continued)

*Primary Examiner* — Reza Ghafoorian
(74) *Attorney, Agent, or Firm* — Birch, Stewart, Kolasch & Birch, LLP

(57) ABSTRACT

Disclosed are a medium for mammalian somatic cells with which mammalian somatic cells can be grown effectively when the mammalian somatic cells are cultured, while reducing the amount of serum to be added to the medium as much as possible or without adding serum thereto, and an additive to constitute the medium. By blending of a ligand for an endothelial cell differentiation gene (Edg) family receptor and a ligand for a serotonin receptor to a medium, somatic cells of mammals can be grown even in cases where the medium does not contain serum at all or contains only a small amount thereof.

17 Claims, 11 Drawing Sheets
(4 of 11 Drawing Sheet(s) Filed in Color)

(56) References Cited

OTHER PUBLICATIONS

European Search Report issued Nov. 7, 2011, in European Patent Application No. 08868742.1.

Floege et al., "Infusion of Platelet-derived Growth Factor or Basic Fibroblast Growth Factor Induces Selective Glomerular Mesangial Cell Proliferation and Matrix Accumulation in Rats", J. Clin. Invest., vol. 92, Dec. 1993, pp. 2952-2962.

Hahn et al., "Induction of Connective Tissue Growth Factor by Activation of Heptahelical Receptors", The Journal of Biological Chemistry, vol. 275, No. 48, Issue of Dec. 1, pp. 37429-37435, 2000.

Inoue et al., "Lysophosphatidic Acid and Platelet-Derived Growth Factor Synergistically Stimulate Growth of Cultured Rat Mesangial Cells," P.S.E.M.B. (1997) vol. 216, pp. 370-379.

Moolenaar et al., "Lysophosphatidic Acid: A Bioactive Phospholipid with Growth Factor-Like Properties," Rev. Physiol. Biochem. Pharmacol. (1992) vol. 119, pp. 47-65.

Reiser et al., "Lysophosphatidic acid-mediated signal-transduction pathways involved in the induction of the early-response genes prostaglandin G/H . . . ," Biochem. J. (1998) vol. 330, pp. 1107-1114.

Shahrestanifar et al., "Lysophosphatidic Acid Activates NF-kB if Fibroblasts," J. Biol. Chem., (Feb. 5, 1999) vol. 274, No. 6, pp. 3828-3833.

Siehler et al., "Sphingosine 1-Phosphate Activates Nuclear Factor-kB through Edg Receptors," J. Biol Chem. (Dec. 28, 2001) vol. 276, No. 52, pp. 48733-48739.

* cited by examiner

Differentiation of hMADS cells into adipocytes and osteocytes

Differentiation of hMSC cells into adipocytes and osteocytes

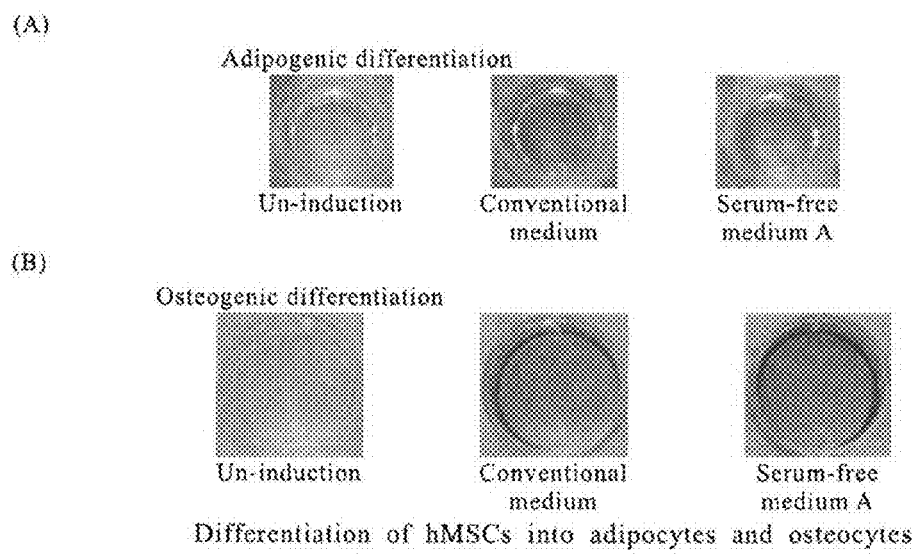
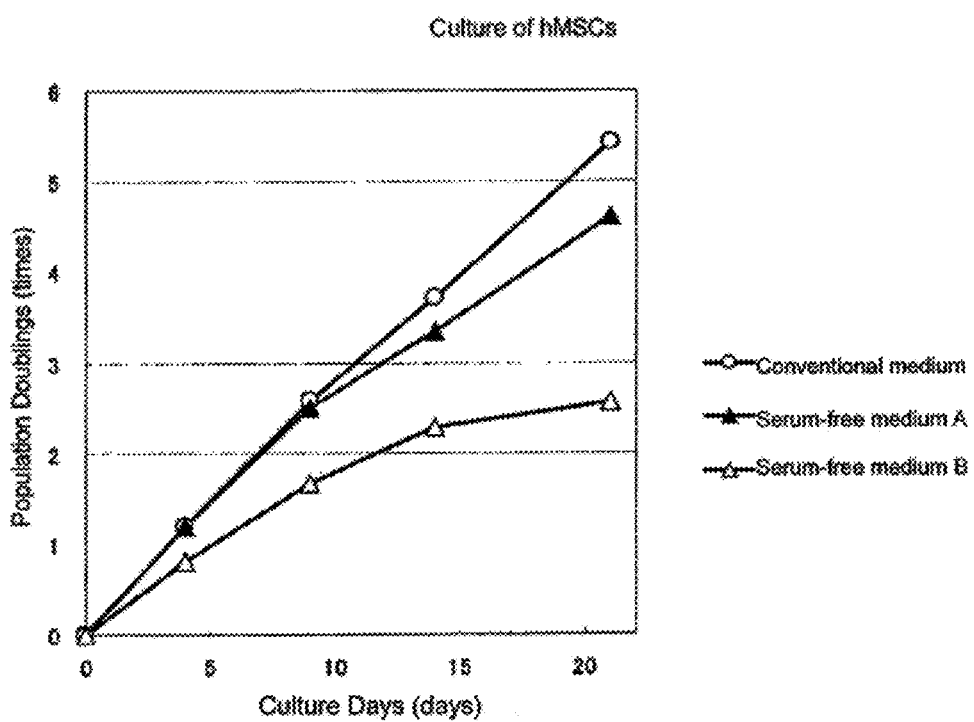

MEDIUM FOR MAMMALIAN SOMATIC CELLS AND ADDITIVE THEREFOR

CROSS-REFERENCE TO RELATED APPLICATIONS

The present application is a Divisional of co-pending U.S. application Ser. No. 12/810,729, filed on Sep. 20, 2010, for which priority is claimed under 35 U.S.C. §120. application Ser. No. 12/810,729 is the national phase of PCT International Application No. PCT/JP2008/073806 filed on Dec. 26, 2008, under 35 U.S.C. §371, which claims priority on JP 2007-340802 filed Dec. 28, 2007, and JP 2008-151295 filed Jun. 10, 2008. The entire contents of each of the above-identified applications are hereby incorporated by reference.

TECHNICAL FIELD

The present invention relates to a medium used when mammalian somatic cells are cultured in vitro, and an additive to constitute the medium.

BACKGROUND ART

Somatic cells of mammals such as human, including cells having pluripotency and differentiated cells are important cells which can be used for cell therapy and regenerative medicine. Culturing of these cells to allow growth thereof is important in view of productivity of cells for cell therapy and promotion of the progress in researches for these medical treatments.

Somatic cells are known to grow in a serum-containing medium to which serum was added to about 10%. As the serum, autologous serum obtained from blood derived from an individual from whom the somatic cells to be cultured were derived, such as one obtained from blood of a patient from whom the somatic cells to be cultured were collected; or serum derived from a different species, such as bovine serum; is usually used.

However, in cases where autologous serum is used, a relatively large amount of blood from the patient is required, so that the burden of the patient is heavy, which is problematic. Further, in cases where serum derived from a different species is used, there is a possibility of contamination of infectious pathogens such as unknown viruses and prions, which is problematic.

Further, in either serum, its component has not been completely elucidated, and the component may vary depending on the origin of the serum used and the lot of a commercial product. Therefore, when the culture is carried out using a large amount of the serum, it is difficult to maintain the quality of the cultured cells obtained, which is problematic.

Therefore, somatic cells are demanded to be grown in a medium wherein serum is not used or the amount of the serum used is reduced as much as possible.

In Japanese Translated PCT Patent Application Laid-open No. 11-506610 (Patent Literature 1), disclosed is a serum-free medium for human mesenchymal cells, containing a minimum essential medium, serum albumin, a compound of iron, insulin and glutamine. It is described that, in this serum-free medium, serotonin which has an activity to promote mitosis of human mesenchymal cells may be added. However, even in cases where mesenchymal cells were cultured in a serum-free medium to which serotonin was added, their growth was relatively slow and cell morphologies changed in a short period of time, leading to decrease in the growing ability, which were problematic.

Japanese Translated PCT Patent Application Laid-open No. 2006-505248 (Patent Literature 2) discloses a serum-free medium for regulation of differentiation of human embryonic stem (ES) cells, which serum-free medium contains a ligand for a lysophospholipid receptor, that is, an endothelial cell differentiation gene (Edg) family receptor, including lysophosphatidic acid (LPA), sphingosine-1-phosphate (S1P) or the like. LPA is also known to have an effect to inhibit differentiation of a preadipocyte to an adipocyte (J. Biol. Chem. Vol. 280, 15, 14656-14662 (2005); Non-patent Literature 1). Further, LPA is also known to have a cell growth-promoting effect (Sci. STKE, Vol. 2005, Issue 292, pp. pe35, 12 Jul. 2005, Non-patent Literature 2; American Journal of Respiratory Cell and Molecular Biology. Vol. 34, pp. 274-285, 2006, Non-patent Literature 3), but the cell growth-promoting effect was confirmed with a serum-containing medium, and a cell growth-promoting effect exerted with a serum-free medium or a low-serum medium containing serum at a concentration of not more than 1% of is not known.

Further, in WO 2007/080919 (Patent Literature 3), a serum-free medium for human bone marrow-derived mesenchymal stem cells is described, and it is described that its culturing condition requires a basic fibroblast growth factor (bFGF), hepatocyte growth factor (HGF), transforming growth factor (TGF-β) and platelet-derived growth factor (PDGF) in addition to an ITS additive (insulin, transferrin and selenium-containing additive), but in cases where the number of the growth factors added was not more than 3, the growing ability is decreased, which was problematic.

It is known that growth of cells of mammals such as human having pluripotency is affected by cytokines and growth factors. Examples thereof include platelet-derived growth factors (PDGFs), basic fibroblast growth factors (bFGFs) and epithelial cell growth factors (EGFs) (Folia Histochemica Et Cytobiological Vol. 44, No. 4, pp. 215-230, 2006, Non-patent Literature 6; J Cell Biochem. Vol. 64, 2, pp. 278-94, 1997, Non-patent Literature 7).

It is known that, during culturing of somatic cells of mammals such as human in vitro, N-acetyl-L-cysteine (NAC) reduces cell death by inhibition of apoptosis (Molecular Human Reproduction Vol. 8, No3.3, pp. 228-236, 2002, Non-patent Literature 8; J Leukoc Biol. Vol. 76, No. 1, pp. 152-61, 2004, Non-patent Literature 9).

[Patent Literature 1] Japanese Translated PCT Patent Application Laid-open No. 11-506610
[Patent Literature 2] Japanese Translated PCT Patent Application Laid-open No. 2006-505248
[Patent Literature 3] WO 2007/080919
[Non-patent Literature 1] J. Biol. Chem. Vol. 280, 15, 14656-14662 (2005)
[Non-patent Literature 2] Sci. STKE, Vol. 2005, Issue 292, p. pe35, 12 Jul. 2005
[Non-patent Literature 3] American Journal of Respiratory Cell and Molecular Biology. Vol. 34, pp. 274-285, 2006
[Non-patent Literature 4] Science. Vol. 294, pp. 1875-1878, 2001 [Non-patent Literature 5] J Biol Chem. Vol. 277, No. 29, pp. 25851-25854, 2002
[Non-patent Literature 6] Folia Histochemica Et Cytobiological Vol. 44, No. 4, pp. 215-230, 2006
[Non-patent Literature 7] J Cell Biochem. Vol. 64, 2, pp. 278-94, 1997
[Non-patent Literature 8] Molecular Human Reproduction Vol. 8, No 3.3, pp. 228-236, 2002
[Non-patent Literature 9] J Leukoc Biol. Vol. 76, No. 1, pp. 152-61, 2004

DISCLOSURE OF THE INVENTION

Problems to be Solved by the Invention

The present invention aims to provide a medium for mammalian somatic cells with which mammalian somatic cells can be grown effectively when the mammalian somatic cells are cultured, while reducing the amount of serum to be added to the medium as much as possible or without adding serum thereto, and to provide an additive to constitute the medium.

Means for Solving the Problems

The present inventors intensively studied to discover that blending of a ligand for an endothelial cell differentiation gene (Edg) family receptor and a ligand for a serotonin receptor to a medium allows effective growth of somatic cells of mammals even in cases where the medium does not contain serum at all or contains only a small amount thereof, thereby completing the present invention.

That is, the present invention provides a medium for mammalian somatic cells, which medium contains a ligand for an endothelial cell differentiation gene (Edg) family receptor and a ligand for a serotonin receptor. Further, the present invention provides an additive for a medium for mammalian somatic cells, which additive contains a ligand for an endothelial cell differentiation gene (Edg) family receptor and a ligand for a serotonin receptor.

Effect of the Invention

The medium and the additive for a medium of the present invention enable efficient growth of somatic cells under conditions where serum, which has been conventionally added to the medium when somatic cells were cultured, is not used or the amount thereof to be added is reduced. Therefore, problems which have occurred by usage of serum, for example, the burden of a patient, contamination of infectious pathogens and the like can be solved. Further, also in cases where serum is added, variations in the growing ability of cells due to variations among the lots of sera to be added can be suppressed. Further, also by using human serum as the serum, somatic cells can be grown efficiently. Further, since somatic cells can be cultured using a reduced amount of serum by the method for culturing of the present invention, cultured somatic cells having a stable quality can be provided. Therefore, the obtained cultured somatic cells can be made to be those having a stable quality wherein the problem of contamination of infectious pathogens is minimized.

BEST MODE FOR CARRYING OUT THE INVENTION

In the present Description, "somatic cells" are cells other than germ cells among the cells constituting a multicellular organism, and include a differentiated cell which was specified to a certain purpose and does not become a cell other than that; and a cell having an ability to differentiate into several types of cells having different functions. The former cell is a functional cell of an adult and includes cells which form various organs in a living body, such as skin cells, nerve cells, muscle cells, blood cells, fibroblasts, hepatic cells, cartilage cells and adipocytes. The latter is called a stem cell and capable of transdifferentiation into one or more types of differentiated cells among the above-described differentiated cells, and includes embryonic stem cells and somatic stem cells. "Somatic stem cells" are cells other than embryonic stem cells among stem cells and precursor cells having an ability to differentiate into several types of cells having different functions, and include induced pluripotent stem cells, hematopoietic stem cells, mesenchymal stem cells, neural stem cells, skin stem cells, hepatic stem cell, pancreatic stem cells and the like.

The cells to be cultured in the medium of the present invention is not restricted as long as they are mammalian somatic cells, and preferred examples thereof include, but are not limited to, somatic stem cells including mesenchymal cells such as fibroblast cells; adipose tissue-derived stem cells; and bone marrow-derived mesenchymal stem cells.

In the medium of the present invention, a ligand for an endothelial cell differentiation gene (Edg) family receptor is contained as an essential component. Here, Edg family receptors are a group of G protein-coupled receptors whose gene sequences are highly homologous to each other, and Edg-1 to Edg-8 have been identified so far in mammals such as human, mouse and sheep (Non-patent Literature 4 and 5). It is known that, among these, Edg-2, Edg-4 and Edg-7 function as LPA receptors, and Edg-1, Edg-3, Edg-5, Edg-6 and Edg-8 function as S1P receptors. "A ligand for a receptor" means a substance which binds specifically to the receptor, and include not only natural ligands existing in a living body but also other naturally-occurring and synthesized compounds known as agonists and antagonists.

As the ligand for an Edg family receptor (this may be hereinafter referred to as "Edg ligand" for convenience), one or more compounds selected from the group consisting of lysophosphatidic acid (LPA) and salts thereof; sphingosine-1-phosphate (S1P); and agonists of Edg family receptors are preferred.

"Agonists of Edg family receptors" means substances which bind to Edg family receptors and act in the same manner as LPA and S1P, and examples thereof include dihydrosphingosine-1-phosphate, platelet-activating factors (PAFs), sphingosine phosphorylcholine, alkyl LPA analogues and FTY720.

LPA is a compound represented by the General Formula (I) below:

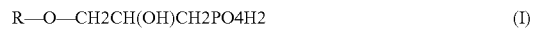

R—O—CH2CH(OH)CH2PO4H2     (I)

(wherein R represents C10-C30 alkyl, C10-C30 alkenyl or C10-C30 acyl).

The number of carbon atoms of acyl group in the group R in the above-described General Formula (I) does not include those of carbonyl.

As the salt of LPA, a known salt may be used, and examples thereof include alkaline metal salts such as sodium salt and potassium salt; and ammonium salt.

Examples of LPA or the salt of LPA include 1-oleoyl lysophosphatidic acid sodium salt and LPA potassium salt.

Edg ligands may be used either individually or in combination of two or more types thereof.

The medium of the present invention further contains a ligand for a serotonin receptor (this may be hereinafter referred to as "serotonin ligand" for convenience). A serotonin receptor is a kind of G protein-binding receptors existing mainly in a central nerve system. As the serotonin ligand, one or more types of compounds selected from serotonin, salts thereof and serotonin agonists are preferred. Serotonin is also called 5-hydroxytryptamine and known to act as a neurotransmitter. A serotonin agonist is a substance known to bind to a serotonin receptor and act in the same manner as serotonin, and examples thereof include ipsapirone, gepirone, buspirone, 1-[2-(4-aminophenyl)ethyl]-4-(3-bifluoromethylphenyl)piperazine (PADD), N,N-dipropyl-5-carboxamidotryptamine (DP-5CT), α-methyl-5-hydroxytryptamine (HT) and 2-methyl-5-HT. As the salt of serotonin, a known salt may be used, and examples thereof include hydrochloride.

Serotonin ligands may be used either individually or in combination of two or more types thereof.

The concentration of the ligand in the medium (in cases where a plurality of the ligands are contained, the total concentration thereof) is usually about 0.01 to 100 μM. In cases where the Edg ligand is at least one selected from the group consisting of lysophosphatidic acid (LPA) and salts thereof, its concentration in the medium is preferably 0.25 to 10 μM. Further, in cases where the Edg ligand is sphingosine-1-phosphate (S1P), its concentration in the medium is preferably 0.01 μM to 0.2 μM. Further, the concentration of the serotonin ligand (in cases where a plurality of the ligands are contained, the total concentration thereof) is preferably 0.1 to 100 μM, more preferably 0.25 to 20 μM.

The medium of the present invention preferably further contains an antioxidant. Preferred examples of the antioxidant include at least one selected from the group consisting of N-acetylcysteine (NAC), L-cysteine, catalase, superoxide dismutase and 2-mercaptoethanol, more preferably, at least one selected from the group consisting of N-acetylcysteine and L-cysteine. These antioxidants are known to have an action to inhibit apoptosis and therefore effective for maintenance and growth of cultured cells. The antioxidants may be used either individually or in combination of two or more types thereof.

The concentration of the antioxidant in the medium (in cases where a plurality of the antioxidants are contained, the total concentration thereof) is preferably 0.01 mM to 10 mM, more preferably 0.1 mM to 1 mM.

The medium of the present invention preferably further contains an animal serum albumin. Albumin is a major component of serum and known to play roles such as deliver of a drug in blood. By containing an animal serum albumin, growth of cultured cells is further promoted. Preferred examples of the animal serum albumin include human serum albumin (HSA) and recombinant human serum albumin (rHSA), and bovine serum albumin (BSA). These albumins may be used either individually or in combination of two or more types thereof.

The concentration of albumin in the medium (in cases where a plurality of the albumins are contained, the total concentration thereof) is preferably 0.0001 to 10% by weight, more preferably 0.0001 to 1% by weight.

The medium of the present invention preferably further contains a growth factor. By containing a growth factor, growth of cultured cells is further promoted. Preferred examples of the growth factor include epidermal growth factors (EGFs), insulin-like growth factor (IGFs), transforming growth factors (TGFs), nerve growth factors (NGFs), brain-derived neurotrophic factors (BDNFs), vascular endothelial cell growth factors (VEGFs), granulocyte colony-stimulating factors (G-CSFs), granulocyte-macrophage colony-stimulating factors (GM-CSFs), erythropoietin (EPO), thrombopoietin (TPO) and hepatocyte growth factors (HGFs), and more preferred examples thereof include platelet-derived growth factors (PDGFs), basic fibroblast growth factors (bFGFs) and epidermal growth factors (EGFs). These growth factors themselves are well-known in the field. The growth factors may be used either individually or in combination of two or more types thereof. Especially, since by containing only two types of growth factors, that is, a platelet-derived growth factor (PDGF) and a basic fibroblast growth factor (bFGF), growth of mesenchymal stem cells can be sufficiently attained, these two types of growth factors are enough for a medium used for culturing mesenchymal stem cells as the growth factors to be included in the medium.

The medium of the present invention may further contain a ligand (PDGF) for a platelet-derived growth factor receptor (PDGFR), and especially, a medium for culturing mesenchymal stem cells preferably contains this. PDGFR is a kind of tyrosine kinase-related receptors, and by containing a ligand for this, mesenchymal stem cells can be grown efficiently. Examples of ligands for PDGFR include PDGF-AA, PDGF-AB, PDGF-BB, PDGF-CC and PDGF-DD, all of which are well-known. The ligands for PDGFR may be used either individually or in combination of two or more types thereof.

The medium of the present invention may contain a ligand (FGF) for a basic fibroblast growth factor receptor, and especially, a medium for culturing mesenchymal stem cells preferably contains this. FGFR is known to mainly exist in mesenchymal cells, and by containing a ligand for this, the life time of a mesenchymal stem cell can be improved. A total of not less than 20 types of ligands for PDGFR are known to exist, which ligands include basic fibroblast growth factors (bFGFs) and acidic fibroblast growth factors (aFGFs). Examples thereof include FGF-1 and FGF-4. Especially, bFGF is known to be strongly involved in formation of tissues. All of these are well-known.

The concentration of the growth factor (in cases where a plurality of the growth factors are contained, the total concentration thereof) is preferably 0.1 to 100 ng/mL, more preferably 1 to 10 ng/mL.

The medium of the present invention may further contain a surfactant. It is considered that, by containing a surfactant at a low concentration, there is an effect to reduce an adverse effect on cell membrane. On the other hand, it is known that addition of a surfactant at a high concentration to a medium induces inhibition of cell growth, and cell death. As the surfactant, nonionic surfactants such as polyoxyethylenesorbitan fatty acid ester (trade names: Tween 20, Tween 40, Tween 60, Tween 80 and the like), alkylphenoxy polyethylene glycol (trade names: Triton X-100 and the like), alkylphenyl polyethylene glycol (trade names: Triton X-114, NP-40 and the like) are preferred. The surfactants may be used either individually or in combination of two or more types thereof.

The concentration of the surfactant (in cases where a plurality of the surfactants are contained, the total concentration thereof) is usually 0.1 to 100 ng/mL, preferably 1 to 10 ng/mL.

The medium of the present invention may contain serum like a normal medium for mammalian cells does, but, since by containing both an Edg ligand and a serotonin ligand, cells can be grown efficiently even in a medium without serum or with a low concentration of serum, the present invention is most useful in cases where the medium is a serum-free medium or a low-serum medium. That is, the content of serum in the medium of the present invention is preferably 0 to 5% by weight, more preferably 0 to 1% by weight, with respect to the total amount of the medium. Within the scope of the present Description and claims, a medium is referred to as a low-serum medium in cases where it contains serum but the content thereof is not more than 5% by weight, preferably 1% by weight.

The medium of the present invention may be the same as a known medium for mammalian cells except that it contains the above-described Edg ligand and serotonin ligand, and preferably further one or more of the above-described antioxidants, animal serum albumins, growth factors and surfactants. Therefore, basically, the medium of the present invention can be obtained by addition of the above-described two essential components and, preferably, further one or more of the above-described preferred components to a known basal medium, preferably to a serum-free or low-serum basal medium.

Examples of known serum-free basal media include minimum essential media (MEM) such as Eagle's medium; Dulbecco's modified Eagle's medium (DMEM), minimum essential medium α (MEM-α); mesenchymal stem cell basal medium (MSCBM); Ham's F-12 and F-10 media; DMEM/F12 medium; Williams medium E; RPMI-1640 medium; MCDB medium; 199 medium; Fisher medium; Iscove's modified Dulbecco's medium (IMDM); and McCoy modified medium.

The medium of the present invention may further contain various additives which are well-known as additives to be contained in a medium for mammalian cells. Examples of such well-known additives include amino acids, inorganic salts and vitamins, as well as other additives such as carbon sources and antibiotics.

Examples of the amino acids include glycine, L-alanine, L-arginine, L-asparagine, L-aspartic acid, L-cysteine, L-cystine, L-glutamate, L-glutamine, L-histidine, L-isoleucine, L-leucine, L-lysine, L-methionine, L-phenylalanine, L-proline, L-serine, L-threonine, L-tryptophan, L-tyrosine and L-valine.

Examples of the inorganic salts include calcium chloride, copper sulfate, iron (III) nitrate, iron sulfate, magnesium chloride, magnesium sulfate, potassium chloride, sodium hydrogen carbonate, sodium chloride, disodium hydrogen phosphate, sodium dihydrogen phosphate, zinc sulfate and selenic acid.

Examples of the vitamins include choline, vitamin A, vitamin B1, vitamin B2, vitamin B3, vitamin B4, vitamin B5, vitamin B6, vitamin B7, vitamin B12, vitamin B13, vitamin B15, vitamin B17, vitamin Bh, vitamin Bt, vitamin Bx, vitamin C, vitamin D, vitamin E, vitamin F, vitamin K, vitamin M and vitamin P.

Addition of these additives to media for mammalian cells itself is known, and the amount of each additive to be added may be the same as that for known media, or it may be set as appropriate by a routine experiment. For example, the amount of each amino acid to be added is usually about 5 mg/L to 500 mg/L, preferably about 10 mg/L to 400 mg/L; the amount of each inorganic salt to be added is usually about 0 mg/L to 10 g/L, preferably 0.01 mg/L to 7 g/L; and the amount of each vitamin to be added is about 0.01 mg/L to 500 mg/L, preferably about 0.05 mg/L to 300 mg/L.

Examples of other additives include (1) growth factors such as corticosterone and progesterone; (2) antibiotics such as penicillin, streptomycin, gentamycin and kanamycin; (3) carbon sources such as glucose, galactose, fructose and sucrose; (4) trace metals such as magnesium, iron, zinc, calcium, potassium, sodium, copper, selenium, cobalt, tin, molybdenum, nickel and silicon; and other additives such as adenosine 5'-monophosphate, corticosterone, ethanolamine, insulin, reduced glutathione, lipoic acid, hypoxanthine, phenol red, progesterone, putrescine, pyruvic acid, thymidine, triiodothyronine, transferrin and lactoferrin. The amount of each of these additives to be added may also be the same as that in conventional use, or may be set as appropriate by a routine experiment depending on the purpose of each additive. It is usually 0.001 mg/L to 5 g/L, especially about 0.1 to 3 g/L.

The medium of the present invention can be used for culturing for growth and maintenance of somatic cells, and in cases where the cells to be cultured are stem cells, it can also be used for induction of differentiation of the stem cells. In cases where it is used for induction of differentiation of stem cells, a differentiation inducer is further added. Examples of the differentiation inducer include cytokines (e.g., various interleukins, erythropoietin and thrombopoietin), colony-stimulating factors (e.g., G-CSF), steroid hormones (e.g., dexamethasone), indoles (e.g., indomethacin), and thiazolidine derivatives (e.g., Rosiglitazone). These may be used either individually or in combination of two or more types thereof. The amount of each differentiation inducer to be added may also be the same as that in conventional use, and it is usually added in an amount of about $1\times10$-10 to $1\times10$-6% by weight with respect to the total amount of the medium.

The medium of the present invention may contain one or more of the above-described various additives, and usually contains a combination of a plurality of additives.

Culturing itself of mammalian somatic cells in the medium of the present invention can be carried out by a method which is the same as one used conventionally, and is usually carried out at 30 to 37° C. under 5% $CO_2$ and 5 to 21% $O_2$.

The present invention also provides an additive to constitute the above-described medium of the present invention. Therefore, the additive of the present invention contains the above-described Edg ligand and serotonin ligand. Further, it preferably contains the above-described various preferred components. Further, it may contain one or more of the above-described various additive(s). As the additive of the present invention, one having a composition which gives the above-described medium of the present invention when dissolved into water or a basal medium is convenient and preferred. In this case, the ratio of each blended component to be contained in the additive is the same as that of the content of the component in the medium. Examples of the basal medium include the above-described various media which are conventionally used for culturing of mammalian cells.

The present invention will now be described more concretely by way of Examples. However, the present invention is not restricted to the Examples below. "%" means "% by weight" unless otherwise specified, and the concentration of each additive means its final concentration in a medium. Therefore, for example, "low-serum medium C to which 2.5 ng/mL basic fibroblast growth factor (bFGF) was added" means that bFGF was added to low-serum medium C such that the final concentration of bFGF is 2.5 ng/mL.

EXAMPLE 1

Culturing of Human Multipotent Adipose-Derived Stem (hMADS) Cells (1-1) Production of Ligands As the serotonin ligand, ligand 1 (S-1) was produced by dissolving 2.1 mg of serotonin hydrochloride (manufactured by Sigma) into 10 mL of DMEM (manufactured by LONZA). Further, as the Edg ligand, ligand 2 (S-2) was produced by dissolving 2.3 mg of 1-oleyl lysophosphatidic acid sodium salt (LPA: manufactured by CAYMAN) into 10 mL of PBS. Further, ligand 3 (S-3) was produced by dissolving 2.1 mg of serotonin hydrochloride and 2.3 mg of LPA into 10 mL of PBS.

(1-2) Growth of hMADS Cells

To a medium containing amino acids (all the amino acids described above), inorganic salts (all the inorganic salts described above), vitamins (all the vitamins described above) and other additives (adenosine 5'-monophosphate, corticosterone, ethanolamine, D-galactose, D-glucose, insulin, reduced glutathione, lipoic acid, hypoxanthine, phenol red, progesterone, putrescine, pyruvic acid, thymidine, triiodothyronine and transferrin), 7×10-4% 2-mercaptoethanol (2-Me), 100 U/mL penicillin/streptomycin (manufactured by GIBCO), 0.5% fetal calf serum (FCS) and 2.5 ng/mL basic fibroblast growth factor (bFGF) were added to obtain low-serum medium C.

S-1 and/or S-2 produced in (1-1) was/were added to low-serum medium C at various concentrations to obtain low-serum media. More particularly, S-1 and/or S-2 was/were added at the concentration(s) below:

a low-serum medium prepared by adding 0% S-1 and 0.2% S-2 to low-serum medium C (0.2% S-2);

a low-serum medium prepared by adding 0.001% S-1 and 0.2% S-2 to low-serum medium C (0.2% S-2, 0.001% S-1);

a low-serum medium prepared by adding 0.01% S-1 and 0.2% S-2 to low-serum medium C (0.2% S-2, 0.01% S-1);

a low-serum medium prepared by adding 0.1% S-1 and 0.2% S-2 to low-serum medium C (0.2% S-2, 0.1% S-1);

a low-serum medium prepared by adding 1% S-1 and 0.2% S-2 to low-serum medium C (0.2% S-2, 1% S-1);

a low-serum medium prepared by adding 10% S-1 and 0.2% S-2 to low-serum medium C (0.2% S-2, 10% S-1);

a low-serum medium prepared by adding 0.1% S-1 and 0% S-2 to low-serum medium C (0.1% S-1);

a low-serum medium prepared by adding 0.1% S-1 and 0.002% S-2 to low-serum medium C (0.1% S-1, 0.002% S-2);

a low-serum medium prepared by adding 0.1% S-1 and 0.02% S-2 to low-serum medium C (0.1% S-1, 0.02% S-2);

a low-serum medium prepared by adding 0.1% S-1 and 0.2% S-2 to low-serum medium C (0.1% S-1, 0.2% S-2);

a low-serum medium prepared by adding 0.1% S-1 and 0.5% S-2 to low-serum medium C (0.1% S-1, 0.5% S-2);

a low-serum medium prepared by adding 0.1% S-1 and 1% S-2 to low-serum medium C (0.1% S-1, 1% S-2);

a low-serum medium prepared by adding 0.1% S-1 and 2% S-2 to low-serum medium C (0.1% S-1, 2% S-2);

a low-serum medium prepared by adding 1% S-1 and 0% S-2 to low-serum medium C (1% S-1);

a low-serum medium prepared by adding 0% S-1 and 1% S-2 to low-serum medium C (1% S-2); and a low-serum medium prepared by adding 1% S-1 and 1% S-2 to low-serum medium C (1% S-1, 1% S-2).

Here, 1% S-1 corresponds to about 10 µM, and 1% S-2 corresponds to about 5 µM.

To DMEM/F12, added were 1% nonessential amino acids (manufactured by GIBCO), 7×10-4% 2-ME, 100 U/L penicillin/streptomycin, 10% FCS and 2.5 ng/mL bFGF to obtain a conventional serum-containing medium (conventional medium).

In a culture dish having a diameter of 100 mm, 10 mL of each of these media was placed, and hMADS were seeded at an initial cell number of 10,000 cells/mL, followed by culturing at 37° C. under 5% CO2.

Changes in the population doubling numbers (n) during the first 21 days after the beginning of the culture were calculated from the results of measurement of the cell numbers at each passage culture using a hemacytometer. The population doubling number means the number of times (n) cell division occurred. During cell division, a cell is divided into two cells, so that the number of cells becomes 2n after n times of division. The population doubling number can be calculated by the following equation.

Population doubling number (n)=Log(2) [number of cells counted at P1/number of cells seeded at P1)×(number of cells counted at P2/number of cells seeded at P2)× . . . ]

(wherein P1, P2, . . . represent the first passage, second passage, . . . , respectively.)

Since an increase of 1 in the population doubling number means a two times larger number of cells and an increase of 2 therein means a four times larger number of cells, an increase of x in the population doubling number means a 2x times larger number of cells.

The results are shown in FIGS. 1 to 3.

FIG. 1 shows changes in the population doubling number observed when the concentration of S-2 was constant.

In FIG. 1, the population doubling numbers for the conventional medium (○); low-serum medium C (▲); 0.2% S-2 (×); 0.2% S-2, 0.001% S-1 (−); 0.2% S-2, 0.01% S-1 (*); 0.2% S-2, 0.1% S-1 (+); 0.2% S-2, 1% S-1 (Δ); and 0.2% S-2, 10% S-1 (♦) are shown.

FIG. 2 shows changes in the population doubling number observed when the concentration of S-1 was constant.

In FIG. 2, the population doubling numbers for the conventional medium (○); low-serum medium C (▲); 0.1% S-1 (×); 0.1% S-1, 0.002% S-2 (−); 0.1% S-1, 0.02% S-2 (*); 0.1% S-1, 0.2% S-2 (+); 0.1% S-1, 0.5% S-2 (Δ); 0.1% S-1, 1% S-2 (♦); and 0.1% S-1, 2% S-2 (◇) are shown.

Further, the results obtained by addition of S-3 to 1% in the above-described low-serum medium C are shown in FIG. 3.

In FIG. 3, the population doubling numbers for the conventional medium (○); 1% S-1 (♦); 1% S-2 (■); and 1% S-3 (●) are shown.

(1-3) Adipogenic Differentiation of hMADS Cells

Cells maintained for several passages using the conventional medium in (1-2) and a medium prepared by adding S-3 to low-serum medium C were transferred to a 96-well culture plate containing 0.1 mL of an adipocyte differentiation medium (DMEM, 10% FCS, 500 µM isobutylmethylxanthine (IBMX), 1 µM dexamethasone, 1 µM insulin, 1 Rosiglitazone) at a cell density of 21,000 cells/cm2, and cultured at 37° C. under 5% CO2 for 10 days, to induce differentiation into adipocytes. Differentiation into adipocytes was confirmed by Oil Red O staining. The results are shown in FIG. 4(A).

(1-4) Osteogenic Differentiation of hMADS Cells

Cells maintained for several passages using the conventional medium in (1-2) and a medium prepared by adding S-3 to low-serum medium C were transferred to a 24-well culture plate containing 0.5 mL of a bone cell-differentiation medium (DMEM, 10% FCS, 200 µM ascorbic acid, 0.1 µM dexamethasone, 10 mM β-glycerophosphate) at a cell density of 10,000 cells/cm2, and cultured at 37° C. under 5% CO2 for 15 days, to induce differentiation into osteocytes. differentiate cell were confirmed by alizarin red S staining. The results are shown in FIG. 4(B).

From the results in FIG. 4, it can be seen that hMADS cells cultured in a medium prepared by adding S-3 to low-serum medium C were stained to the same extent as the cells cultured in the conventional medium containing 10% serum, and hence that the hMADS cells differentiated into adipocytes and osteocytes to the same extent. Therefore, it can be seen that the both cells cultured in these media have an ability to maintain the undifferentiated state, and that there is no difference in differentiation potential as stem cells.

Further, it was confirmed that the tendencies in growth and differentiation shown in FIGS. 1 to 4 did not change even in the case where human serum was used instead of FCS used in (1-2).

EXAMPLE 2

Culturing of Human Bone Marrow-derived Mesenchymal Stem Cells (hMSCs)

(2-1) Production of Ligands

As the serotonin ligand, ligand 1 (S-1) was produced by dissolving 2.1 mg of serotonin hydrochloride (manufactured by Sigma) into 10 mL of DMEM (manufactured by LONZA).

Further, as the Edg ligand, ligand 2 (S-2) was produced by dissolving 2.3 mg of 1-oleyl lysophosphatidic acid sodium salt (LPA: manufactured by CAYMAN) into 10 mL of PBS, and ligand 2 (S-2') was produced by dissolving 1.9 mg of sphingosine-1-phosphate (S1P: manufactured by CAYMAN) into 10 mL of DMEM.

Further, ligand 3 (S-3) was produced by dissolving 2.1 mg of serotonin hydrochloride and 2.3 mg of LPA into 10 mL of PBS.

(2-2) Growth of hMSCs

Low-serum medium C1 was obtained by adding 100 U/mL penicillin/streptomycin (manufactured by GIBCO) and 0.5% FCS to a basal medium which was the same as the basal medium prepared in Example 1 except that it did not contain hypoxanthine and thymidine and a part of the inorganic salts (copper sulfate, iron (III) nitrate, iron sulfate, magnesium chloride, disodium hydrogen phosphate, zinc sulfate). Further, low-serum medium C2 was obtained by adding 100 U/mL penicillin/streptomycin (manufactured by GIBCO) and 1.0% FCS to the basal medium.

S-1 and/or 2 produced in (2-1) was/were added to low-serum medium C1 at various concentrations to obtain low-serum media. More particularly, S-1 and/or S-2 was/were added at the concentration(s) below:

a low-serum medium prepared by adding 0% S-1 and 0.2% S-2 to low-serum medium C1 (0.2% S-2);

a low-serum medium prepared by adding 0.001% S-1 and 0.2% S-2 to low-serum medium C1 (0.2% S-2, 0.001% S-1);

a low-serum medium prepared by adding 0.01% S-1 and 0.2% S-2 to low-serum medium C1 (0.2% S-2, 0.01% S-1);

a low-serum medium prepared by adding 0.1% S-1 and 0.2% S-2 to low-serum medium C1 (0.2% S-2, 0.1% S-1);

a low-serum medium prepared by adding 1% S-1 and 0.2% S-2 to low-serum medium C1 (0.2% S-2, 1% S-1);

a low-serum medium prepared by adding 10% S-1 and 0.2% S-2 to low-serum medium C1 (0.2% S-2, 10% S-1);

a low-serum medium prepared by adding 0.1% S-1 and 0% S-2 to low-serum medium C1 (0.1% S-1);

a low-serum medium prepared by adding 0.1% S-1 and 0.002% S-2 to low-serum medium C1 (0.1% S-1, 0.002% S-2);

a low-serum medium prepared by adding 0.1% S-1 and 0.02% S-2 to low-serum medium C1 (0.1% S-1, 0.02% S-2);

a low-serum medium prepared by adding 0.1% S-1 and 0.2% S-2 to low-serum medium C1 (0.1% S-1, 0.2% S-2);

a low-serum medium prepared by adding 0.1% S-1 and 1% S-2 to low-serum medium C1 (0.1% S-1, 1% S-2);

a low-serum medium prepared by adding 0.1% S-1 and 2% S-2 to low-serum medium C1 (0.1% S-1, 2% S-2);

a low-serum medium prepared by adding 1% S-1 and 0% S-2 to low-serum medium C1 (1% S-1);

a low-serum medium prepared by adding 0% S-1 and 1% S-2 to low-serum medium C1 (1% S-2);

a low-serum medium prepared by adding 1% S-1 and 1% S-2 to low-serum medium C1 (1% S-1, 1% S-2); and a low-serum medium prepared by adding 0.5% FCS, 1% S-1 and 1% S-2 to low-serum medium C1 (1% S-3, 1% FCS).

S-1 and/or 2' produced in (2-1) was/were added to low-serum medium C2 at various concentrations to obtain low-serum media. More particularly, S-1 and/or S-2' was/were added at the concentration(s) below:

a low-serum medium prepared by adding 1% S-1 and 0.1% S-2' to low-serum medium C2 (0.1% S-2', 1% S-1);

a low-serum medium prepared by adding 1% S-1 and 0.02% S-2' to low-serum medium C2 (0.02% S-2', 1% S-1);

a low-serum medium prepared by adding 1% S-1 and 0.01% S-2' to low-serum medium C2 (0.01% S-2', 1% S-1);

a low-serum medium prepared by adding 1% S-1 and 0.002% S-2' to low-serum medium C2 (0.002% S-2', 1% S-1); and a low-serum medium prepared by adding 1% S-1 and 0.0002% S-2' to low-serum medium C2 (0.0002% S-2', 1% S-1).

A medium kit for human mesenchymal stem cells containing 10% FCS, L-glutamine and antibiotics (hMSC Bullet Kit, manufactured by LONZA) was used as the conventional medium.

In a culture dish having a diameter of 100 mm, 10 mL of each of these media was placed, and hMSCs were seeded at an initial cell number of 10,000 cells/mL, followed by culturing at 37° C. under 5% CO2.

FIGS. 5 to 7 show changes in the population doubling numbers (n) during the first 19 days after the beginning of the culture, and FIG. 8 shows changes in the population doubling numbers (n) during the first 18 days after the beginning of the culture, calculated using the results obtained by measurement of the cell numbers at each passage using a hemacytometer. The results are shown in FIGS. 5 to 8.

FIG. 5 shows changes in the population doubling number observed when the concentration of S-2 was constant.

In FIG. 5, the population doubling numbers for the conventional medium (○); low-serum medium C1 (▲); 0.2% S-2 (×); 0.2% S-2, 0.001% S-1 (−); 0.2% S-2, 0.01% S-1 (*); 0.2% S-2, 0.1% S-1 (+); 0.2% S-2, 1% S-1 (Δ); 0.2% S-2, 10% S-1 (◆); 1% S-1 (□); 1% S-2 (■); and 1% S-1, 1% S-2 (●) are shown.

FIG. 6 shows changes in the population doubling number observed when the concentration of S-1 was constant.

In FIG. 6, the population doubling numbers for the conventional medium (○); low-serum medium C1 (▲); 0.1% S-1 (×); 0.1% S-1, 0.002% S-2 (−); 0.1% S-1, 0.02% S-2 (*); 0.1% S-1, 0.2% S-2 (+); 0.1% S-1, 1% S-2 (◆); 0.1% S-1, 2% S-2 (◇); 1% S-1 (□); 1% S-2 (■); and 1% S-1, 1% S-2 (●) are shown.

Further, the results obtained by addition of S-3 to 1% in the above-described low-serum medium C1 are shown in FIG. 7.

In FIG. 7, the population doubling numbers for the conventional medium (○); low-serum medium C1 (▲); 1% S-1 (◆); 1% S-2 (■); 1% S-3 (●); and 1% S-3, 1% FCS (◇) are shown.

FIG. 8 shows changes in the population doubling number observed when the concentration of S-1 was constant.

In FIG. 8, the population doubling numbers for the conventional medium (○); 0.1% S-2', 1% S-1 (Δ); 0.02% S-2', 1% S-1 (◆); 0.01% S-2', 1% S-1 (■); 0.002% S-2', 1% S-1 (◇); 0.0002% S-2', 1% S-1 (□) are shown.

(2-3) Adipogenic Differentiation of hMSCs

Cells maintained for several passages using the conventional medium in (2-2) and 1% S-3, 1% FCS were transferred to wells in a 96-well plate each containing 0.1 mL of an adipocyte differentiation medium (DMEM, 10% FCS, 500 μM isobutylmethylxanthine (IBMX), 1 μM dexamethasone, 1 μM insulin, 1 μM Rosiglitazone) at a cell density of 20,000 cells/cm2, and cultured at 37° C. under 5% CO2 for 14 days, to induce differentiation into adipocytes. differentiated cells were confirmed by Oil Red O staining. The results are shown in FIG. 9(A).

(2-4) Osteogenic Differentiation of hMSCs

Cells maintained for several passages using the conventional medium in (2-2) and 1% S-3, 1% FCS were transferred to wells in a 24-well plate each containing 0.5 mL of a bone cell differentiation medium (DMEM, 10% FCS, 200 μM ascorbic acid, 0.1 μM dexamethasone, 10 mM β-glycerophosphate) at a cell density of 3,000 cells/cm2, and cultured at 37° C. under 5% CO2 for 14 days, to induce differentiation into osteocytes. Differentiated cells confirmed by alizarin red S staining. The results are shown in FIG. 9(B).

From the results in FIG. 9, it can be seen that hMSCs cultured in 1% S-3, 1% FCS were stained to the same extent as the cells cultured in the conventional medium containing 10% serum, and hence that the hMSCs differentiated into adipocytes and osteocytes to the same extent. Therefore, it can be seen that the both cells cultured in these media have an ability to maintain the undifferentiated state, and that there is no difference in differentiation potential as stem cells.

Further, it was confirmed that the tendencies in growth and differentiation shown in FIGS. 5 to 9 did not change even in the case where human serum was used instead of FCS used in (2-2).

Further, it was confirmed that the tendency in differentiation did not change even in the case where S1P was used instead of LPA as the Edg ligand.

EXAMPLE 3

To a medium containing amino acids (all the amino acids described above), inorganic salts (all the inorganic salts described above), vitamins (all the vitamins described above) and other additives (adenosine 5'-monophosphate, corticosterone, ethanolamine, D-galactose, D-glucose, insulin, reduced glutathione, lipoic acid, hypoxanthine, phenol red, progesterone, putrescine, pyruvic acid, thymidine, triiodothyronine and transferrin), 7×10-4% 2-Me, 100 U/L penicillin/streptomycin, 0.5% FCS, 2.5 ng/mL bFGF and 1% S-3 produced in (1-1) were added to obtain low-serum medium 3 (1% S-3 LS).

Further, the serum-free medium 3 (1% S-3 SF) was obtained with the same composition as that of the above-described low-serum medium 3 except that FCS was not contained.

To DMEM/F12, added were 1 mg/L nonessential amino acids (manufactured by GIBCO), 7×10-4% 2-ME, 100 U/L penicillin/streptomycin, 10% FCS and 2.5 ng/mL bFGF to obtain a conventional serum-containing medium (conventional medium).

In a culture dish having a diameter of 100 mm, 10 mL of each of these media was placed, and hFBs were seeded at an initial cell number of 10,000 cells/mL, followed by culturing at 37° C. under 5% CO2.

Changes in the population doubling numbers (n) during the first 22 days after the beginning of the culture were calculated from the results of measurement of the cell numbers at each passage using a hemacytometer. The results are shown in FIG. 10.

In FIG. 10, the population doubling numbers for the conventional medium (○); 1% S-3 LS (●); and 1% S-3 SF (▲) are shown.

EXAMPLE 4

Effect of Reduction of Differences Among Lots of Sera (Culturing of hMSCs)

(4-1) Production of Ligands

Ligand 3 (S-3) was produced by dissolving 2.1 mg of serotonin hydrochloride and 2.3 mg of LPA into 10 mL of PBS.

(4-2) Growth of hMSC

Each of low-serum media C2 (FCS 1-4) was obtained by adding 100 U/ml penicillin/streptomycin (manufactured by GIBCO) and 1.0% FCS of a different lot to a basal medium which was the same as the basal medium prepared in Example 1 except that it did not contain hypoxanthine and thymidine and a part of the inorganic salts (copper sulfate, iron (III) nitrate, iron sulfate, magnesium chloride, disodium hydrogen phosphate, zinc sulfate).

Further, low-serum media (1% S-3, 1% FCS (1-4)) were obtained by adding 1% S-3 produced in (4-1) to low-serum media C2 (FCS 1-4).

To DMEM, added were L-glutamine, antibiotics, and 10% FCS (1-4) corresponding to the above-described 4 kinds of lots to obtain respective conventional serum-containing media (1% S-3, 1% FCS (1-4)).

In a culture dish having a diameter of 100 mm, 10 mL of each of these media was placed, and hMSCs were seeded at an initial cell number of 10,000 cells/mL, followed by culturing at 37° C. under 5% CO2.

Changes in the population doubling numbers (n) during the first 18 days after the beginning of the culture were calculated from the results of measurement of the cell numbers at each passage using a hemacytometer. Changes in the population doubling numbers observed when different lots of FCS were used are shown in FIGS. 11 to 14. In FIGS. 11 to 14, the conventional media (FCS 1-4) were represented by (○); and the low-serum media (1% S-3, 1% FCS (1-4)) were represented by (●).

Further, a summary of the population doubling numbers (n) observed when culture was carried out for 14 days using the conventional media (FCS 1-4) and the low-serum media (1% S-3, 1% FCS (1-4)) is shown in FIG. 15.

From the results in FIGS. 11 to 15, it can be seen that the influence of differences in production lots of FCS on cell growth is smaller in a low-serum medium (1% S-3, 1% FCS) than in a conventional medium containing 10% serum.

EXAMPLE 5

Culture with Human Serum (Culturing of hMSCs)

(5-1) Production of Ligands

Ligand 3 (S-3) was produced by dissolving 2.1 mg of serotonin hydrochloride and 2.3 mg of LPA into 10 mL of PBS.

(5-2) Growth of hMSC

Each of low-serum media C3 (HS 1, 2) was obtained by adding 100 U/ml penicillin/streptomycin (manufactured by GIBCO) and 1.0% human serum HS of a different lot to a basal medium which was the same as the basal medium prepared in Example 1 except that it did not contain hypoxanthine and thymidine and a part of the inorganic salts (copper sulfate, iron (III) nitrate, iron sulfate, magnesium chloride, disodium hydrogen phosphate, zinc sulfate).

Low-serum media (1% S-3, 1% FCS (1-4)) were obtained by adding 1% S-3 produced in (5-1) to the low-serum media C2 (HS 1, 2).

To DMEM, added were L-glutamine, antibiotics, and 10% HS (1, 2) corresponding to the above-described 2 kinds of lots to obtain respective conventional serum-containing media (1% S-3, 1% FCS (1-4)).

In a culture dish having a diameter of 100 mm, 10 mL of each of these media was placed, and hMSCs were seeded at an initial cell number of 10,000 cells/mL, followed by culturing at 37° C. under 5% CO2.

Changes in the population doubling numbers (n) during the first 18 days after the beginning of the culture were calculated from the results of measurement of the cell numbers at each passage using a hemacytometer. Changes in the population doubling number observed when different lots of HS were used are shown in FIGS. 16 and 17. The conventional media (HS 1, 2) were represented by (○); and the low-serum media (1% S-3, 1% HS (1, 2)) were represented by (●).

From the results in FIGS. 16 and 17, it can be seen that the culture is possible even with the low-serum medium using human serum (1% S-03, 1% HS).

EXAMPLE 6

Culturing of Human Bone Marrow-Derived Mesenchymal Stem Cells (hMSCs) 2

To a basal medium containing amino acids (all the amino acids described above), inorganic salts (all the inorganic salts described above except copper sulfate, iron (III) nitrate, iron sulfate, magnesium chloride, disodium hydrogen phosphate, zinc sulfate), vitamins (all the vitamins described above) and other additives (adenosine 5'-monophosphate, corticosterone, ethanolamine, D-galactose, D-glucose, insulin, reduced glutathione, lipoic acid, phenol red, progesterone, putrescine, pyruvic acid, triiodothyronine and transferrin) in water, 1 ng/ml platelet-derived growth factor (PDGF), 2.5 ng/ml basic fibroblast growth factor (bFGF), 0.02% by weight human serum albumin, 500 μM N-acetylcysteine (NAC), 100 U/ml penicillin/streptomycin (manufactured by GIBCO) and 1% S-3 produced in (1-1) were added to obtain serum-free growth medium A.

A conventional serum-containing medium (conventional medium A) was obtained by adding 100 U/mL penicillin/streptomycin and 10% FBS to DMEM.

In a culture dish having a diameter of 100 mm, 10 mL of each of these media was placed, and hMSCs were seeded at an initial cell number of 15,000 cells/mL, followed by culturing at 37° C. under 5% CO2.

Changes in the population doubling numbers (n) during the first 18 days after the beginning of the culture were calculated from the results of measurement of the cell numbers at each passage using a hemacytometer.

The results are shown in FIG. 18. As shown in FIG. 18, culturing in serum-free growth medium A of the present invention gave the population doubling numbers equivalent to those in the case of culturing in the serum-containing conventional medium A even though serum-free growth medium A is serum-free and contains only two types of growth factors.

Adipogenic Differentiation of hMSCs

Cells maintained for several passages using conventional medium A and serum-free growth medium A were transferred to wells in a 48-well plate each containing 0.3 mL of an adipocyte differentiation medium (DMEM, 10% FCS, 500 μM IBMX, 1 μM dexamethasone, 1 μM insulin, 1 μM Rosiglitazone) at a cell density of 30,000 cells/cm2, and cultured at 37° C. under 5% CO2 for 14 days, to induce differentiation into adipocytes. differentiated cells were confirmed by Oil Red O staining.

The results are shown in FIG. 19(A). As shown in FIG. 19(A), in the case of maintaining the cells in serum-free growth medium A of the present invention for several passages followed by differentiation induction, the cells were stained to a slightly lesser extent than, although about the same extent as, in the case of culturing in serum-containing conventional medium A, so that evident differentiated cells were confirmed.

Osteogenic Differentiation of hMSCs

Cells maintained for several passages using serum-free growth medium A was transferred to wells in a 12-well plate each containing 0.7 mL of a bone cell differentiation medium (DMEM, 10% FCS, 200 μM ascorbic acid, 0.1 μM dexamethasone, 10 mM β-glycerophosphate) at a cell density of 3,000 cells/cm2, and cultured at 37° C. under 5% CO2 for 21 days, to induce differentiation into Osteocytes. Differentiated cellswere confirmed by alizarin red S staining.

The results are shown in FIG. 19(B). As shown in FIG. 19(B), in the case of maintaining the cells in serum-free growth medium A of the present invention for several passages followed by differentiation induction, the cells were stained to the same extent as in the case of culturing in conventional serum-containing medium A, so that differentiated cells confirmed.

EXAMPLE 7

Culturing of Human Bone Marrow-Derived Mesenchymal Stem Cells (hMSCs) 3

To a basal medium containing amino acids (all the amino acids described above), inorganic salts (all the inorganic salts described above except copper sulfate, iron (III) nitrate, iron sulfate, magnesium chloride, disodium hydrogen phosphate, zinc sulfate), vitamins (all the vitamins described above) and other additives (adenosine 5'-monophosphate, corticosterone, ethanolamine, D-galactose, D-glucose, insulin, reduced glutathione, lipoic acid, phenol red, progesterone, putrescine, pyruvic acid, triiodothyronine and transferrin) in water, 0.02% by weight human serum albumin, 500 μM N-acetylcysteine (NAC), 100 U/ml penicillin/streptomycin (manufactured by GIBCO) and 1% S-3 produced in (1-1) were added to obtain serum-free growth medium B.

In a culture dish having a diameter of 100 mm, 10 mL of each of the obtained serum-free growth medium B, and serum-free growth medium A and conventional medium A prepared in Example 6 was placed, and hMSCs were seeded at an initial cell number of 20,000 cells/mL, followed by culturing at 37° C. under 5% CO2.

Changes in the population doubling numbers (n) during the first 21 days after the beginning of the culture were calculated from the results of measurement of the cell numbers at each passage using a hemacytometer.

The results are shown in FIG. 20. As shown in FIG. 20, even in the case where the cells were cultured in the serum-free growth medium B of the present invention which did not contain a growth factor, the cells could be grown, although the population doubling numbers were smaller than in the cases of culturing in serum-free medium B of the present invention containing growth factors and culturing in conventional medium A.

Adipogenic Differentiation of hMSCs

Cells maintained for several passages using conventional medium A or serum-free growth medium A or serum-free growth medium B were transferred to wells in a 48-well plate each containing 0.3 mL of an adipocyte differentiation medium (DMEM, 10% FCS, 500 μM IBMX, 1 μM dexamethasone, 1 μM insulin, 1 μM Rosiglitazone) at a cell density of 30,000 cells/cm2, and cultured at 37° C. under 5% CO2 for 14 days, to induce differentiation into adipocytes. Differentiated cells were confirmed by Oil Red O staining.

The results are shown in FIG. 21(A). As shown in FIG. 21(A), the cells cultured for several passages in the respective three types of media followed by differentiation induction were stained to about the same extents, so that even in the case where the cells were cultured in serum-free medium B of the present invention which did not contain a growth factor, differentiation was confirmed to have occurred to the same extent as in the case of culturing in the serum-containing conventional medium.

Osteogenic Differentiation of hMSCs

Cells maintained for several passages using serum-free growth medium A or serum-free growth medium B were transferred to wells in a 12-well plate each containing 0.7 mL of a bone cell differentiation medium (DMEM, 10% FCS, 200 μM ascorbic acid, 0.1 μM dexamethasone, 10 mM β-glycerophosphate) at a cell density of 3,000 cells/cm2, and cultured at 37° C. under 5% CO2 for 21 days, to induce differentiation into bone cells. Differentiated cells were confirmed by alizarin red S staining.

The results are shown in FIG. 21(A). As shown in FIG. 21(A), in the case of maintaining the cells in serum-free growth medium A or serum-free growth medium B for several passages followed by differentiation induction, the cells were stained to the same extent as in the case of culturing in conventional medium A, so that differentiation into bone cells was confirmed. It was revealed that the serum-free growth medium of the present invention allows osteocytes to keep an ability to differentiate into osteocytes even in cases where it does not contain a growth factor.

The patent or application file contains at least one color drawing. Copies of this patent or patent application publication with color drawing will be provided by the USPTO upon request and payment of the necessary fee.

BRIEF DESCRIPTION OF THE DRAWINGS

FIG. 19 shows differentiation of the human bone marrow-derived mesenchymal stem cells (hMSCs) obtained in Example 6 into adipocytes (A) and osteocytes (B).

FIG. 20 is a graph showing changes in the population doubling number of the human bone marrow-derived mesenchymal stem cells (hMSCs) obtained in Example 7.

Figure 1:
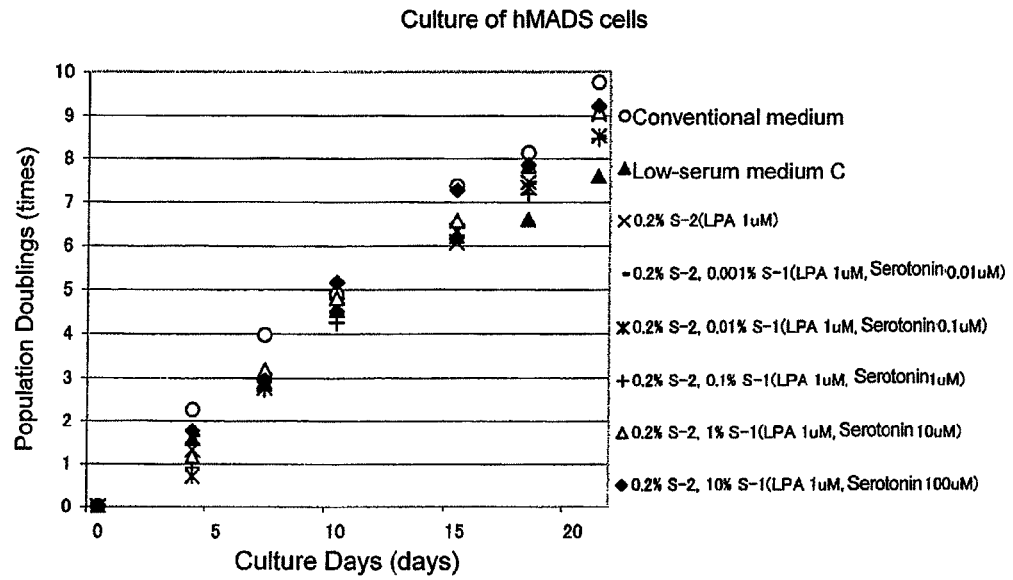
FIG. 1 is a graph showing changes in the population doubling number of the human multipotent adipose-derived stem (hMADS) cells obtained in Example 1.
Figure 2:
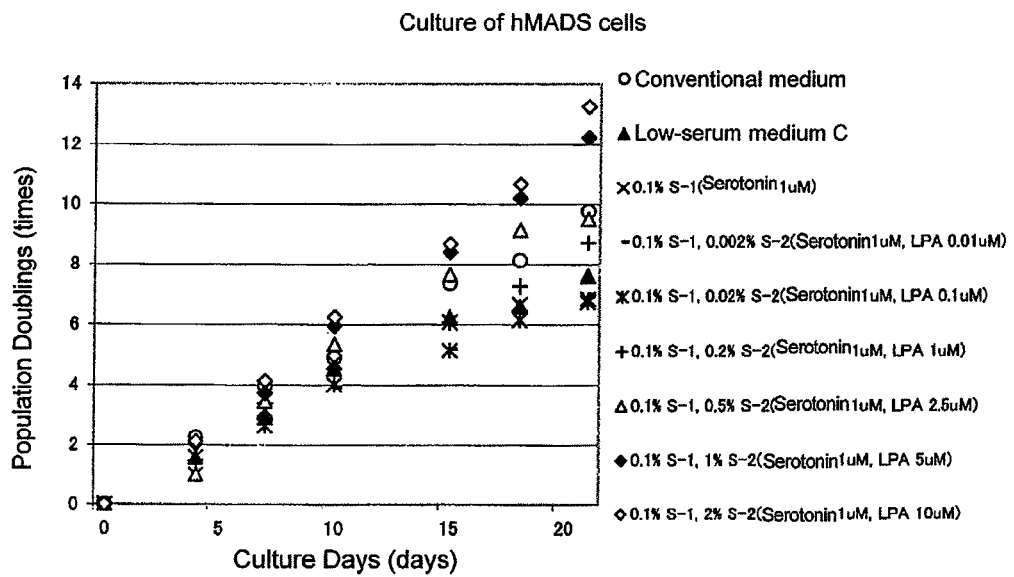
FIG. 2 is a graph showing changes in the population doubling number of the human multipotent adipose-derived stem (hMADS) cells obtained in Example 1.
Figure 3:
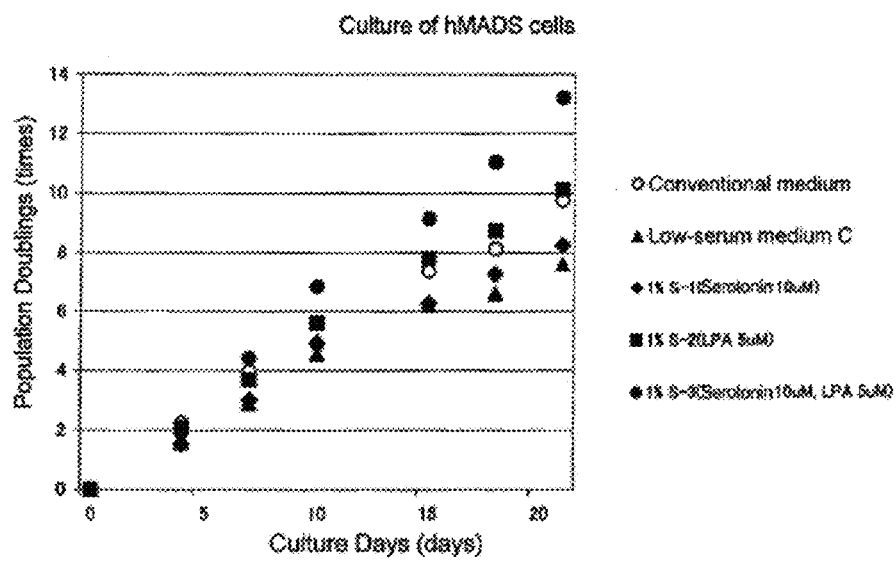
FIG. 3 is a graph showing changes in the population doubling number of the human multipotent adipose-derived stem (hMADS) cells obtained in Example 1.
Figure 4:
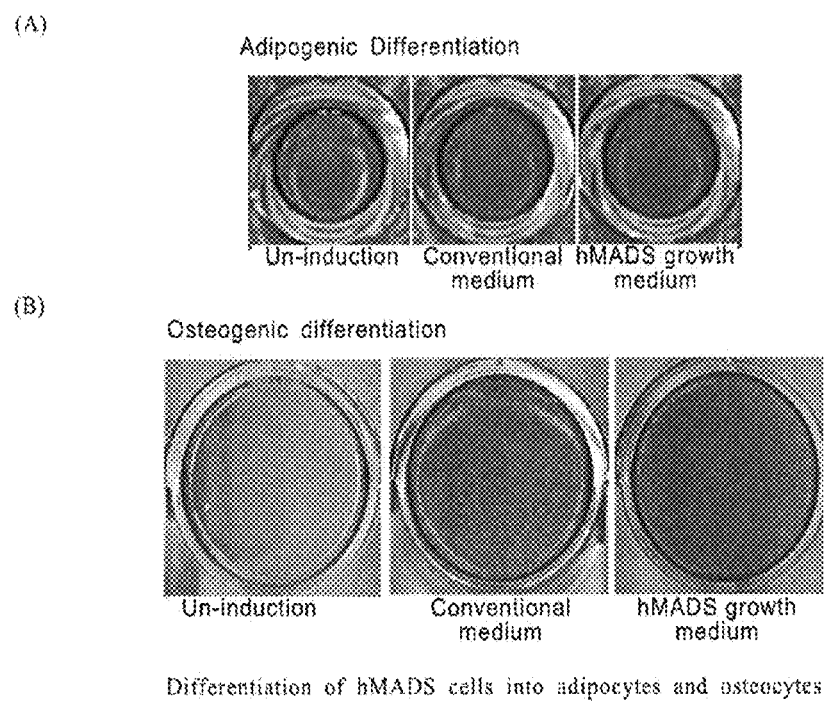
FIG. 4 shows differentiation of human multipotent adipose-derived stem (hMADS) cells into adipocytes (A) and osteocytes (B).
Figure 5:
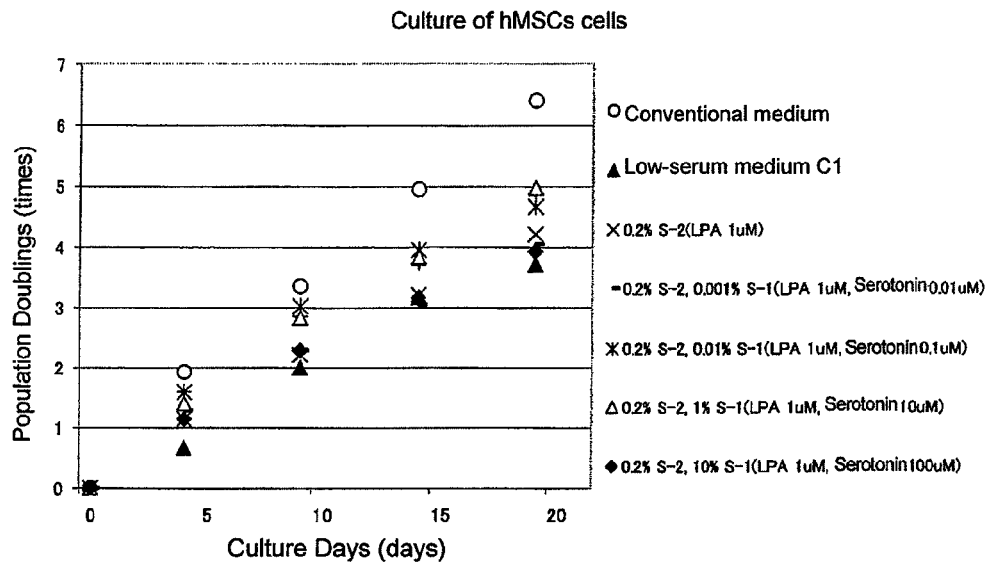
FIG. 5 is a graph showing changes in the population doubling number of the human bone marrow-derived mesenchymal stem cells (hMSCs) obtained in Example 2.
Figure 6:
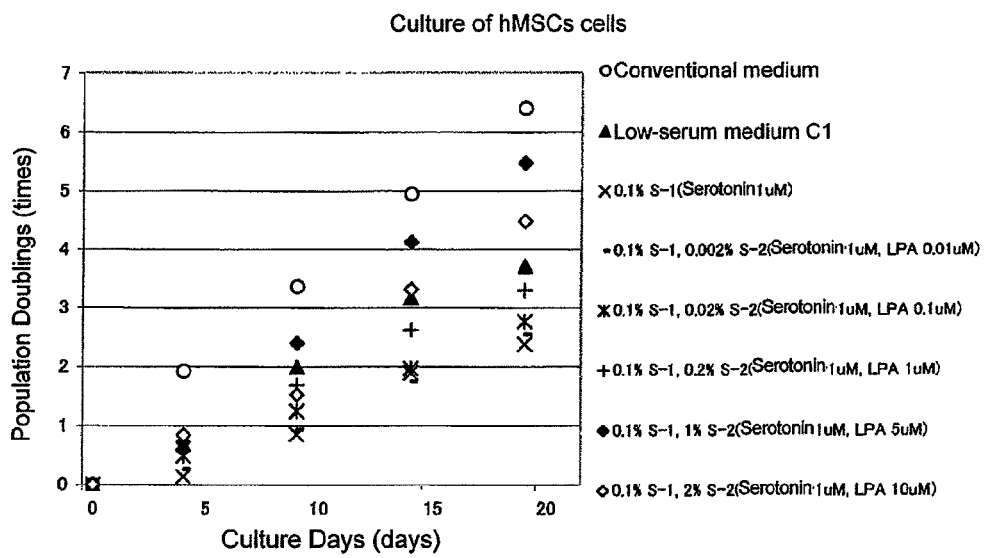
FIG. 6 is a graph showing changes in the population doubling number of the human bone marrow-derived mesenchymal stem cells (hMSCs) obtained in Example 2.
Figure 7:
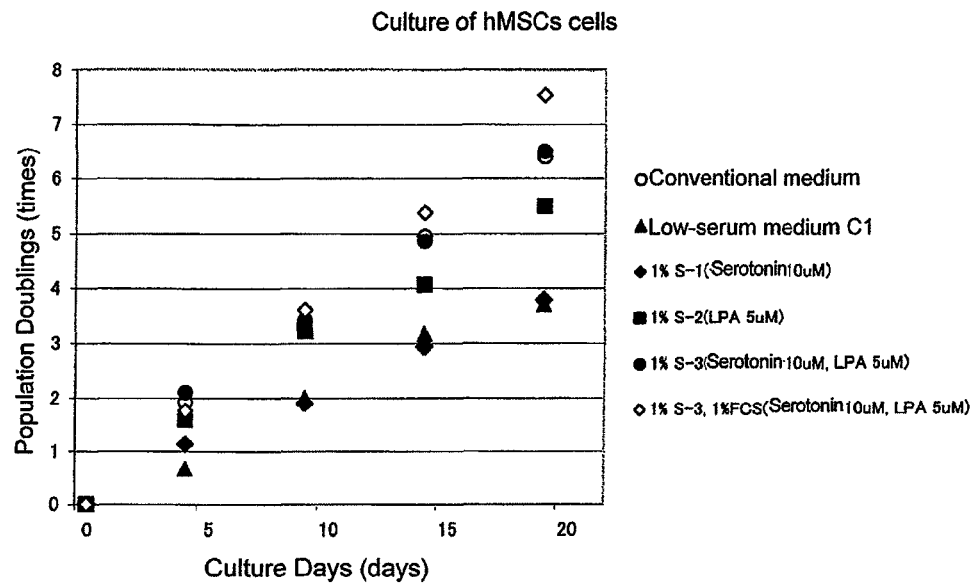
FIG. 7 is a graph showing changes in the population doubling number of the human bone marrow-derived mesenchymal stem cells (hMSCs) obtained in Example 2.
Figure 8:
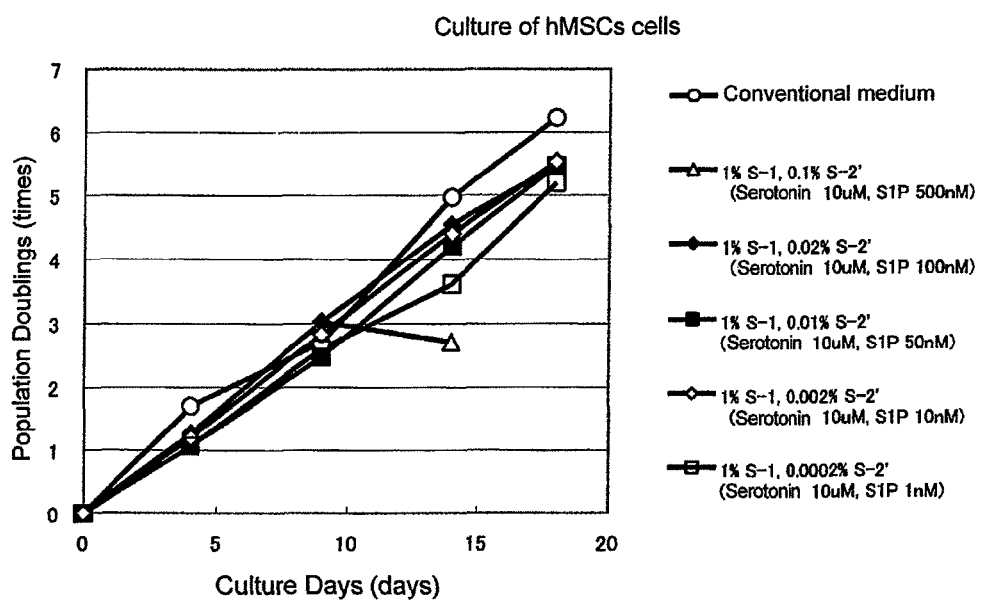
FIG. 8 is a graph showing changes in the population doubling number of the human bone marrow-derived mesenchymal stem cells (hMSCs) obtained in Example 2.
Figure 9:
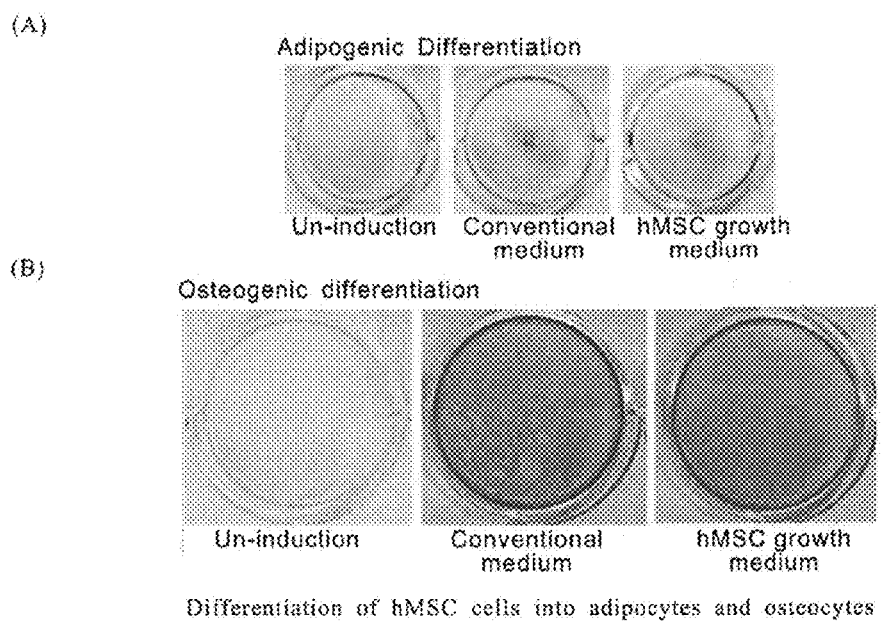
FIG. 9 shows differentiation of human bone marrow-derived mesenchymal stem cells (hMSCs) into adipocytes (A) and osteocytes (B).
Figure 10:
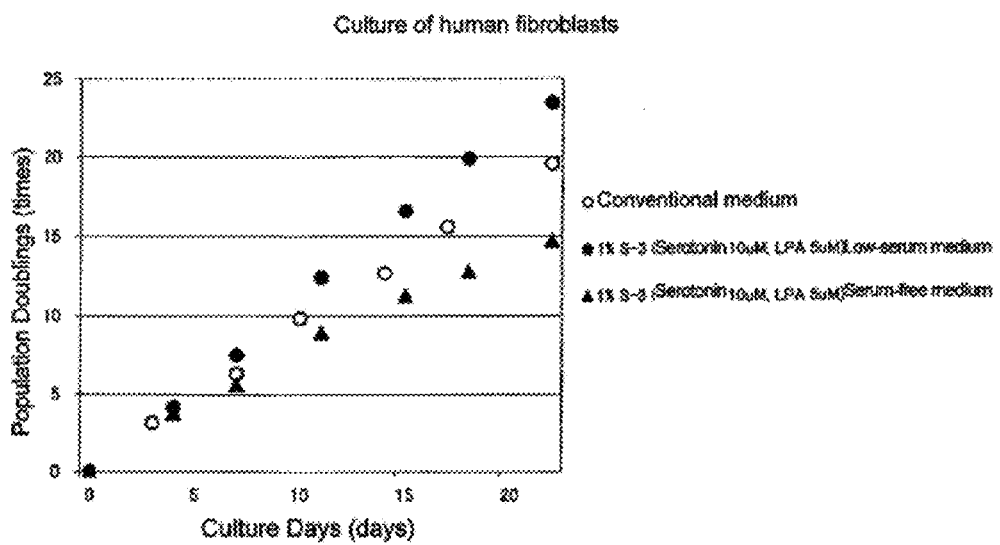
FIG. 10 is a graph showing changes in the population doubling number of the human fibroblasts (hFBs) obtained in Example 3.
Figure 11:
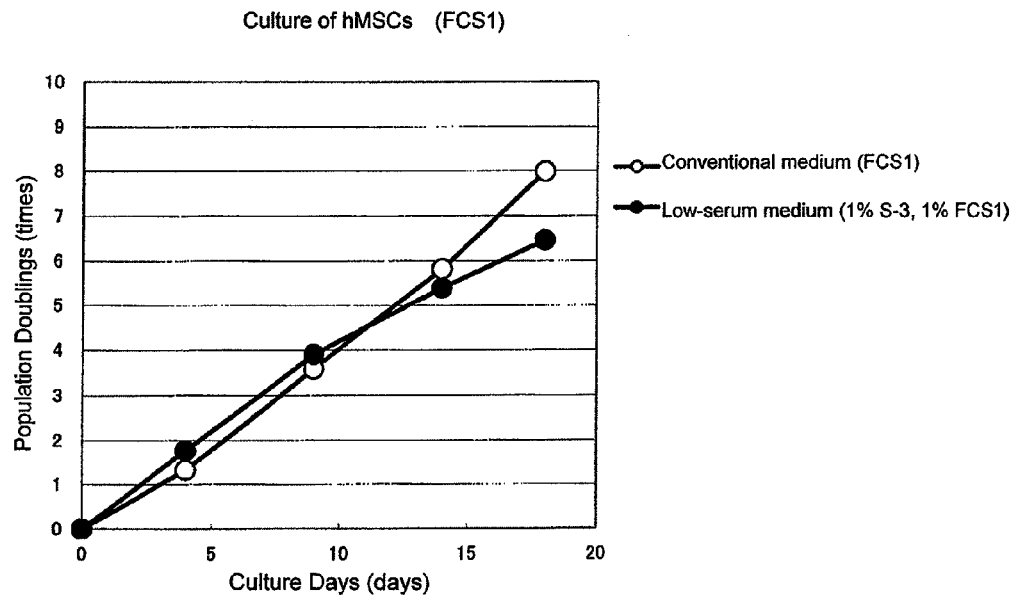
FIG. 11 is a graph showing changes in the population doubling number of the human bone marrow-derived mesenchymal stem cells (hMSCs) obtained in Example 4.
Figure 12:
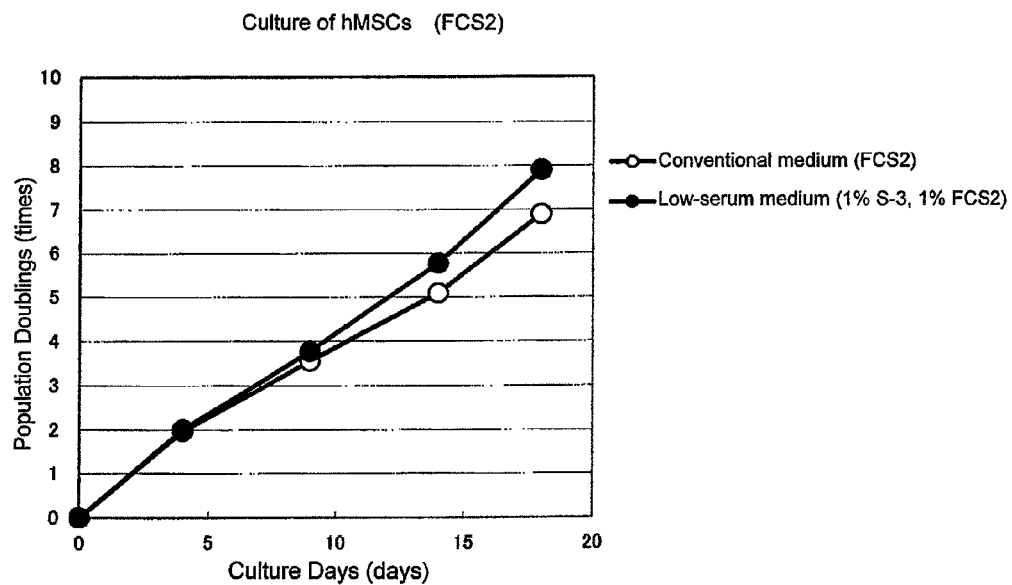
FIG. 12 is a graph showing changes in the population doubling number of the human bone marrow-derived mesenchymal stem cells (hMSCs) obtained in Example 4.
Figure 13:
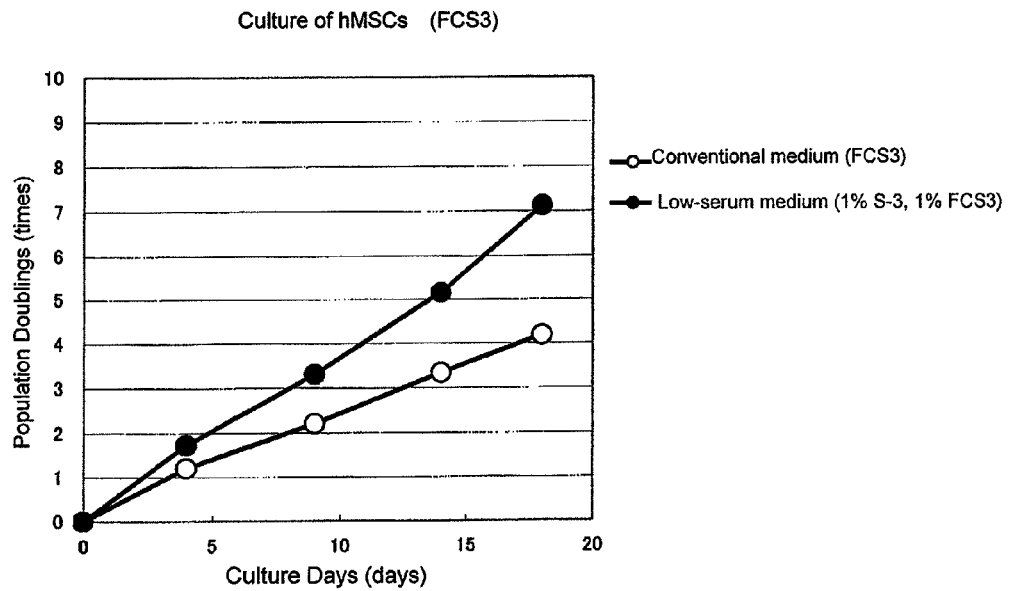
FIG. 13 is a graph showing changes in the population doubling number of the human bone marrow-derived mesenchymal stem cells (hMSCs) obtained in Example 4.
Figure 14:
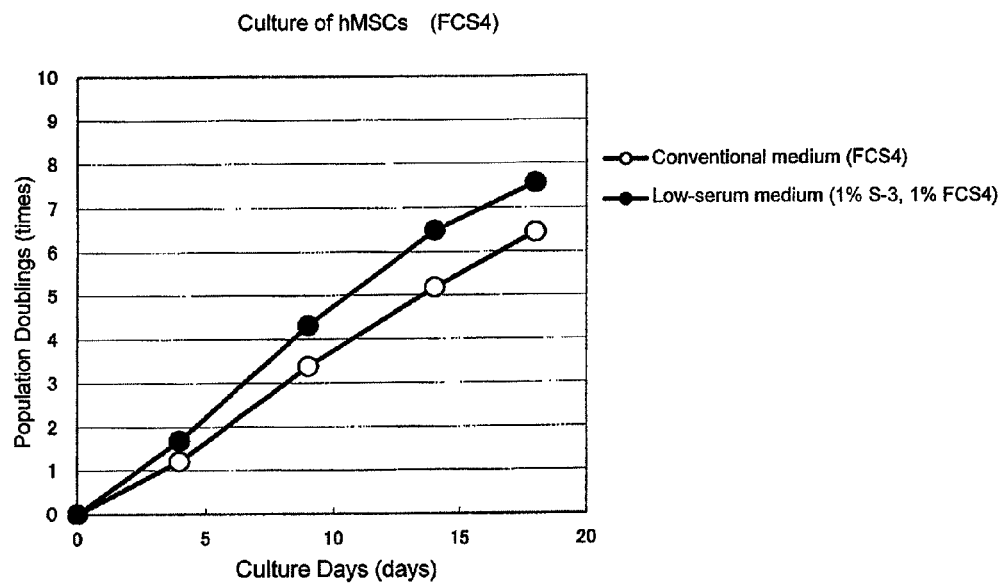
FIG. 14 is a graph showing changes in the population doubling number of the human bone marrow-derived mesenchymal stem cells (hMSCs) obtained in Example 4.
Figure 15:
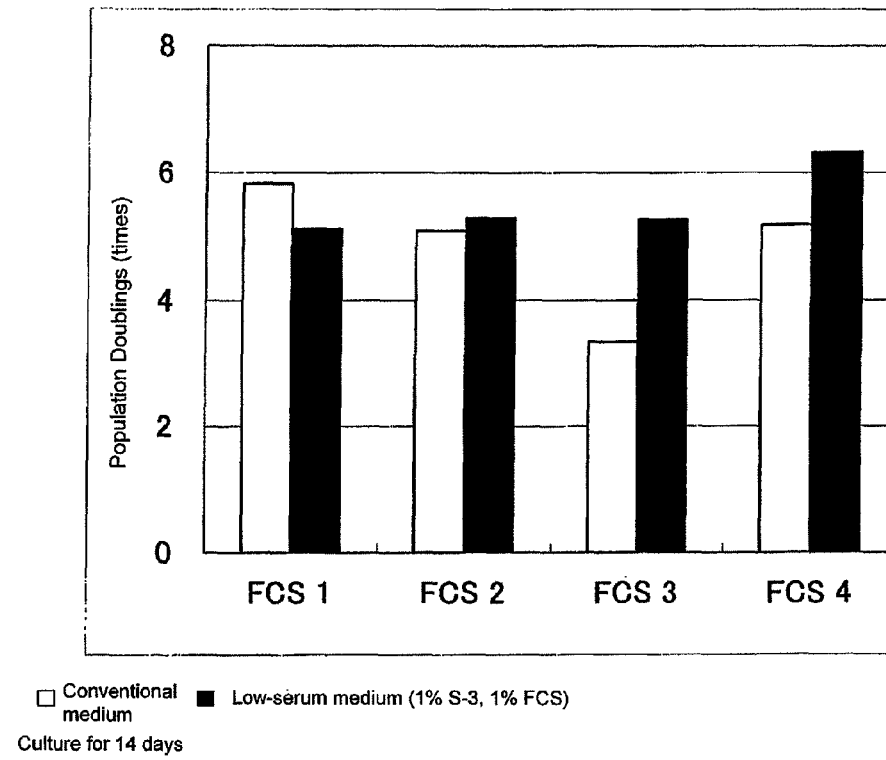
FIG. 15 is a diagram showing the population doubling numbers of the human bone marrow-derived mesenchymal stem cells (hMSCs) obtained in Example 4, which were cultured in respective media containing fetal calf serum (FCS) of different lots for 14 days.
Figure 16:
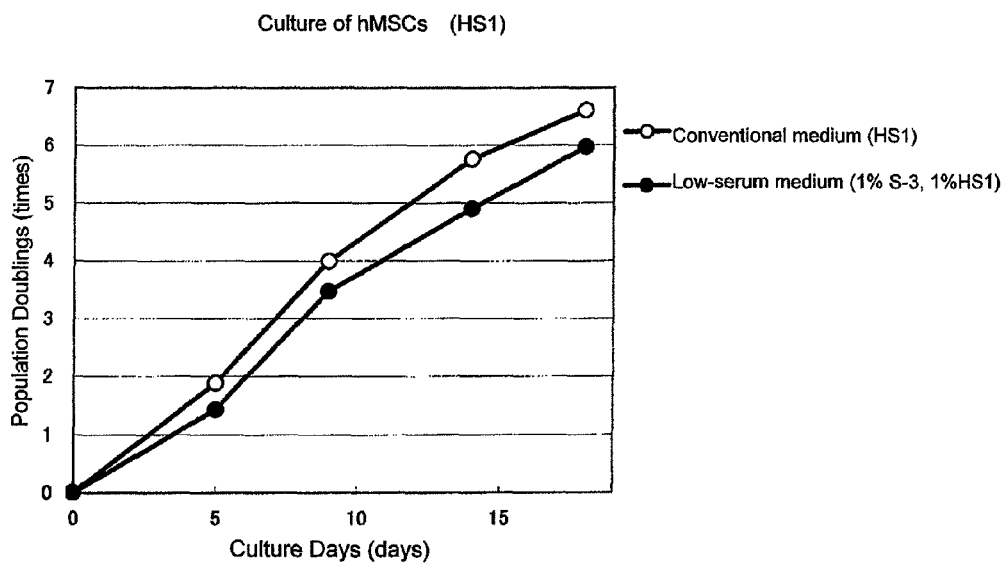
FIG. 16 is a graph showing changes in the population doubling number of the human bone marrow-derived mesenchymal stem cells (hMSCs) obtained in Example 5 cultured in human serum-containing media.
Figure 17:
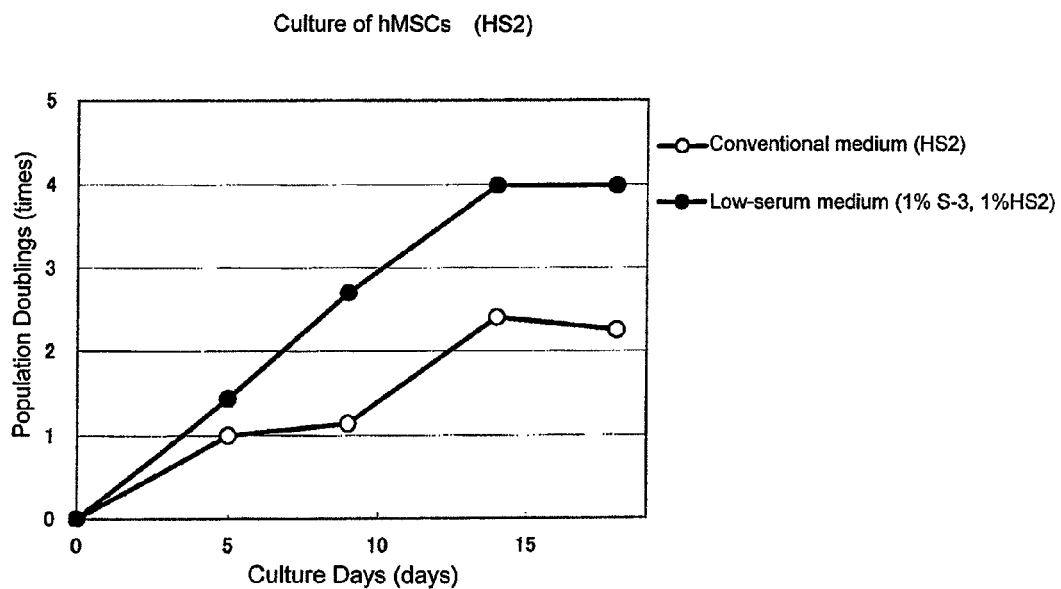
FIG. 17 is a graph showing changes in the population doubling number of the human bone marrow-derived mesenchymal stem cells (hMSCs) obtained in Example 5 cultured in human serum-containing media.
Figure 18:
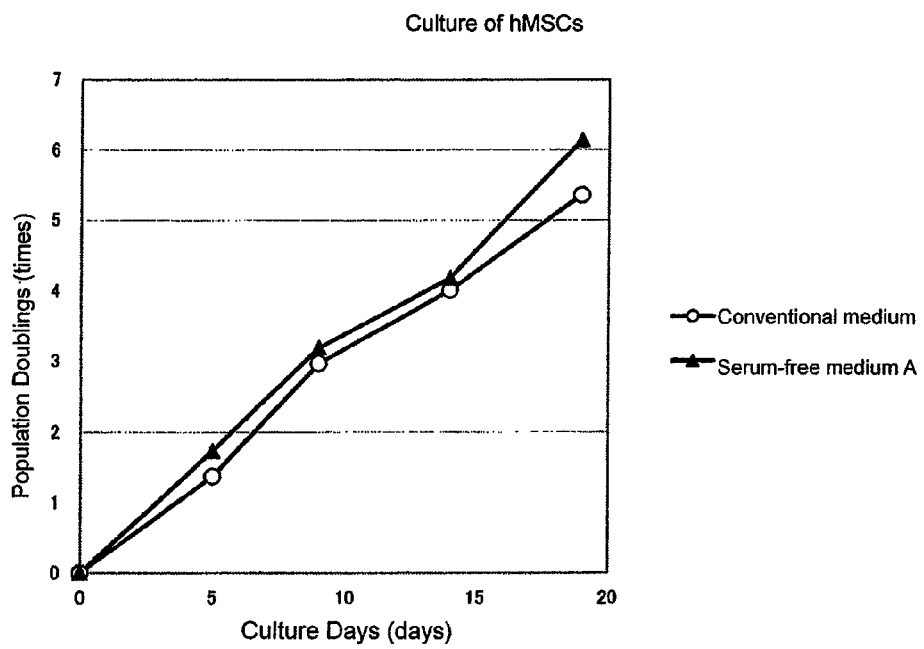
FIG. 18 is a graph showing changes in the population doubling number of the human bone marrow-derived mesenchymal stem cells (hMSCs) obtained in Example 6.
Figure 21:
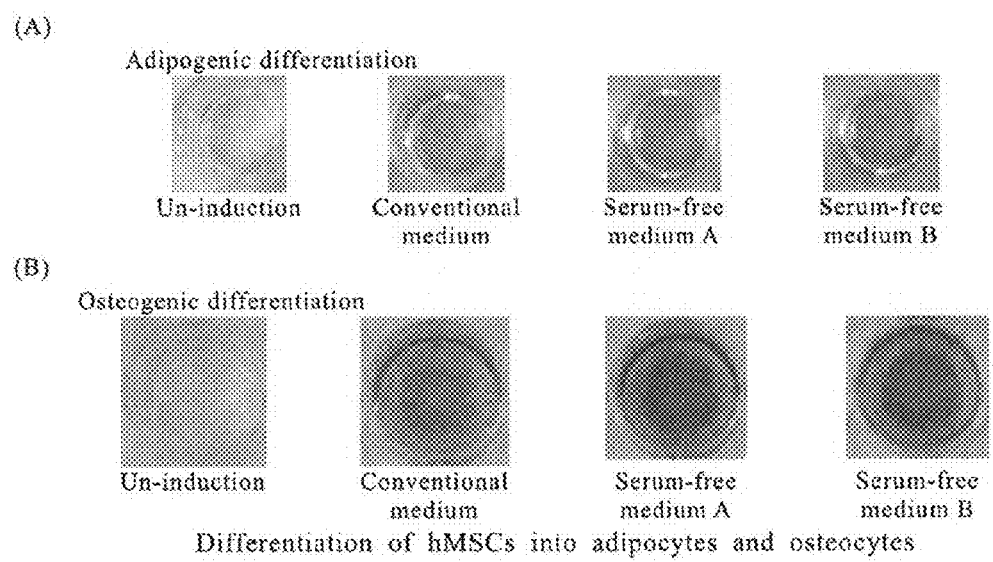
FIG. 21 shows differentiation of the human bone marrow-derived mesenchymal stem cells (hMSCs) obtained in Example 7 into adipocytes (A) and osteocytes (B).

The invention claimed is:

1. A method of passage-culturing mammalian mesenchymal cells, said method comprising culturing of the mammalian mesenchymal cells in a serum-free medium, wherein the serum-free medium comprises an agonist for an endothelial cell differentiation gene (Edg) family receptor and an agonist for a serotonin receptor, and
   wherein passage-culturing of the mammalian cells in serum-free medium is for more than four days.

2. The method according to claim 1, wherein the concentration of said agonist for an endothelial cell differentiation gene family receptor in the medium is 0.01 to 100 μM, and the concentration of said agonist for a serotonin receptor in the medium is 0.1 to 100 μM.

3. The method according to claim 1, wherein said agonist for an endothelial cell differentiation gene family receptor is at least one selected from the group consisting of lysophosphatidic acid (LPA) and salts thereof; sphingosine-1-phosphate (S1P); and agonists of endothelial cell differentiation gene (Edg) family receptors.

4. The method according to claim 1, wherein said agonist for an endothelial cell differentiation gene family receptor is at least one selected from the group consisting of lysophosphatidic acid (LPA) and salts thereof and has a concentration of 0.25 to 10 µM in the medium, and said agonist for a serotonin receptor has a concentration of 0.25 to 20 µM in the medium.

5. The method according to claim 1, wherein said agonist for a serotonin receptor is at least one selected from the group consisting of serotonin and salts thereof; and agonists of serotonin receptors.

6. The method according to claim 1, further comprising an antioxidant.

7. The method according to claim 1, wherein said antioxidant is at least one selected from the group consisting of N-acetylcysteine and L-cysteine.

8. The method according to claim 6, wherein the concentration of said antioxidant is 0.01 mM to 10 mM.

9. The method according to claim 1, further comprising an animal serum albumin.

10. The method according to claim 1, wherein the concentration of said serum albumin in the medium is 0.0001 to 10% by weight.

11. The method according to claim 1, further comprising a growth factor.

12. The method according to claim 11, wherein said growth factor is at least one selected from the group consisting of platelet-derived growth factors (PDGFs), basic fibroblast growth factors (bFGFs) and epidermal growth factors (EGFs).

13. The method according to claim 12, comprising two types of said growth factors which are a platelet-derived growth factor (PDGF) and a basic fibroblast growth factor (bFGF) in the medium.

14. The method according to claim 11, wherein the concentration of said growth factor in the medium is 0.1 to 100 ng/mL.

15. The method according to claim 1, wherein the mesenchymal cells are bone marrow-derived mesenchymal stem cells.

16. The method according to claim 1, wherein the mesenchymal cells are adipose tissue-derived stem cells.

17. The method according to claim 1, wherein the mesenchymal cells are fibroblast cells.

* * * * *